United States Patent
Miao et al.

(10) Patent No.: US 10,515,449 B2
(45) Date of Patent: Dec. 24, 2019

(54) DETECTION OF 3D POSE OF A TEE PROBE IN X-RAY MEDICAL IMAGING

(71) Applicant: Siemens Medical Solutions USA, Inc., Malvern, PA (US)

(72) Inventors: Shun Miao, Bethesda, MD (US); Rui Liao, Princeton Junction, NJ (US); Ryan Spilker, Arlington, MA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 439 days.

(21) Appl. No.: 15/344,210

(22) Filed: Nov. 4, 2016

(65) Prior Publication Data

US 2018/0130200 A1    May 10, 2018

(51) Int. Cl.
| | |
|---|---|
| A61B 5/05 | (2006.01) |
| G06T 7/00 | (2017.01) |
| A61B 8/00 | (2006.01) |
| G06T 7/73 | (2017.01) |
| A61B 6/12 | (2006.01) |
| A61B 6/00 | (2006.01) |
| A61B 8/12 | (2006.01) |

(52) U.S. Cl.
CPC .............. *G06T 7/0012* (2013.01); *A61B 6/12* (2013.01); *A61B 6/5223* (2013.01); *A61B 8/12* (2013.01); *A61B 8/4245* (2013.01); *G06T 7/74* (2017.01); *G06T 2207/10028* (2013.01); *G06T 2207/10116* (2013.01); *G06T 2207/30021* (2013.01); *G06T 2207/30244* (2013.01)

(58) Field of Classification Search
None
See application file for complete search history.

(56) References Cited

U.S. PATENT DOCUMENTS

| | | | |
|---|---|---|---|
| 6,144,759 A | 11/2000 | Weese et al. | |
| 2007/0103464 A1* | 5/2007 | Kaufman | G06T 7/0012 345/424 |
| 2011/0091087 A1* | 4/2011 | Ibarz | G06T 11/006 382/131 |
| 2012/0296202 A1 | 11/2012 | Mountney et al. | |
| 2013/0279780 A1* | 10/2013 | Grbic | A61B 5/0033 382/131 |
| 2015/0223773 A1* | 8/2015 | John | A61B 8/0841 600/424 |

OTHER PUBLICATIONS

King's College London, UoA15—General Engineering: "Robust and Accurate 2D-3D Image Registration." p. 1-4, 2014.
USA Phillips. "EchoNavigator Fusing Live X-ray and Live Echo." Koninklijke Philips N.V., accessed on Sep. 7, 2016.

* cited by examiner

*Primary Examiner* — Joel F Brutus

(57) ABSTRACT

Pose of a probe is detected in x-ray medical imaging. Since the TEE probe is inserted through the esophagus of a patient, the pose is limited to being within the esophagus. The path of the esophagus is determined from medical imaging prior to the intervention. During the intervention, the location in 2D is found from one x-ray image at a given time. The 3D probe location is provided by assigning the depth of the esophagus at that 2D location to be the depth of the probe. A single x-ray image may be used to determine the probe location in 3D, allowing for real-time pose determination without requiring space to rotate a C-arm during the intervention.

20 Claims, 3 Drawing Sheets

DETECTION OF 3D POSE OF A TEE PROBE IN X-RAY MEDICAL IMAGING

BACKGROUND

The present embodiments relate to detection of a probe position from x-ray imaging. Two-dimensional (2D) x-ray imaging (e.g. fluoroscopy) is routinely used for interventional cardiac surgery. x-ray imaging and transesophageal echocardiography (TEE) provide complementary information during the cardiac surgery. x-ray imaging is used to monitor interventional devices (e.g., catheter and TEE probe), and three-dimensional (3D) TEE is used to visualize soft tissue. To fully utilize complementary information from both modalities, the coordinate systems of the x-ray and ultrasound are registered or aligned. Detecting the 3D pose of a TEE probe from x-ray images enables the fusion of x-ray and ultrasound images. With an accurately estimated 3D pose of the TEE probe, measurements or annotations in the ultrasound image or the x-ray image can be transferred to the coordinate system of the other modality.

A challenge in 3D pose detection from single view x-ray image is the ambiguity of depth, which causes largely inaccurate estimation of the object's movement along the viewing axis of the C-arm detector of the x-ray system. Conventional methods to resolve the depth ambiguity typically involve acquiring at least two x-ray images of the TEE probe from different angles (e.g., 30 degrees apart) during the procedure or intervention. However, a bi-plane system to acquire two x-ray images simultaneously is not commonly available due to increased equipment cost, and the additional radiation dose associated with bi-plane acquisition is undesired. For a mono-plane system, once the interventional procedure starts, it is inconvenient and may be impossible to rotate the C-arm to acquire two images at different angles during the procedure because of the density of equipment in the operating room. In addition, real-time TEE probe pose estimation for dynamic fusion of ultrasound and x-ray images becomes impossible when a C-arm needs to be rotated between different angles in order to acquire the x-ray images used to estimate the pose at each given time.

BRIEF SUMMARY

By way of introduction, the preferred embodiments described below include methods, systems, instructions, and computer readable media for detection of a probe pose in x-ray medical imaging. Since the TEE probe is inserted through the esophagus of a patient, the pose is limited to being within the esophagus. The path of the esophagus is determined from medical imaging prior to the intervention. During the intervention, the location in 2D is found from one x-ray image at a given time. The 3D probe location is provided by assigning the depth of the esophagus at that 2D location to be the depth of the probe. A single x-ray image may be used to determine the probe location in 3D, allowing for real-time pose determination without requiring space to rotate a C-arm during the intervention.

In a first aspect, a method is provided for detection of a probe pose in x-ray medical imaging. A three-dimensional path of an esophagus of a patient is determined from medical imaging prior to an intervention on the patient. An orientation and a first location of a trans-esophageal echocardiographic (TEE) probe is detected during the intervention on the patient. The detection is from a single x-ray image. The x-ray image is acquired during the intervention, and the first location is in two dimensions with ambiguity along a third dimension corresponding to a view direction from an x-ray source used for the single x-ray image. The ambiguity along the third dimension is resolved with the three-dimensional path, providing a second location in the three dimensions. Coordinates of the x-ray source are aligned with the TEE probe based on the second location.

In a second aspect, a method is provided for detection of a probe pose in x-ray medical imaging. A trajectory along which a probe is to be inserted into a patient is determined. The trajectory is determined in three-dimensions relative a patient. A location in two dimensions is detected from an individual x-ray image of the patient with the probe within the patient. The location in three dimensions is detected from the detection of the location in the two dimensions from the individual x-ray image and the trajectory. Fused medical imaging is performed with the probe and x-ray imaging based on the location in the three dimensions.

In a third aspect, a system is provided for detection in medical imaging. A transesophageal echocardiography imaging system includes a transducer for imaging with ultrasound from within a patient. An x-ray system is configured to acquire a sequence of x-ray images with an x-ray source in one position relative to the patient during an intervention. The x-ray images represent the patient and the transducer over time. An image processor is configured to detect, separately for each of the x-ray images, a three-dimensional location of the transducer relative to the x-ray source. The three-dimensional location is detected from proximity of (a) a line from the transducer as detected in the x-ray image to the position of the x-ray source to (b) a trajectory of an esophagus of the patient.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Depth ambiguity in 3D pose detection of a TEE probe at a given time is resolved using a single-view x-ray image. The single-view x-ray image and a 3D trajectory of the esophagus are used to resolve the depth ambiguity so that the 3D pose of the TEE probe may be accurately estimated. The human esophagus is a narrow tubular structure. Since a TEE probe is put into the esophagus for imaging, the anatomy of the esophagus (e.g., the centerline) provide cross-sectional location constraints for the TEE probe.

Being able to accurately register the TEE probe using a single-view x-ray image may dramatically improve user experience and may enable dynamic fusion between the echo model and x-ray in real-time. Since x-ray imaging from different directions is not needed during the intervention or treatment procedure, a more seamless workflow for TEE probe tracking and fusion of information between x-ray imaging and ultrasound imaging is provided.

The fusion of x-ray and ultrasound imaging assists many interventional applications, especially for complicated catheter-based structural heart disease (SHD) therapy (e.g., trans-catheter aortic valve repair (TAVR), mitral valve repair (MVR), or left atrial appendage closure (LAAC)). The alignment of the coordinate systems may be used in other cardiac or non-cardiac situations or procedures.

Figure 1:
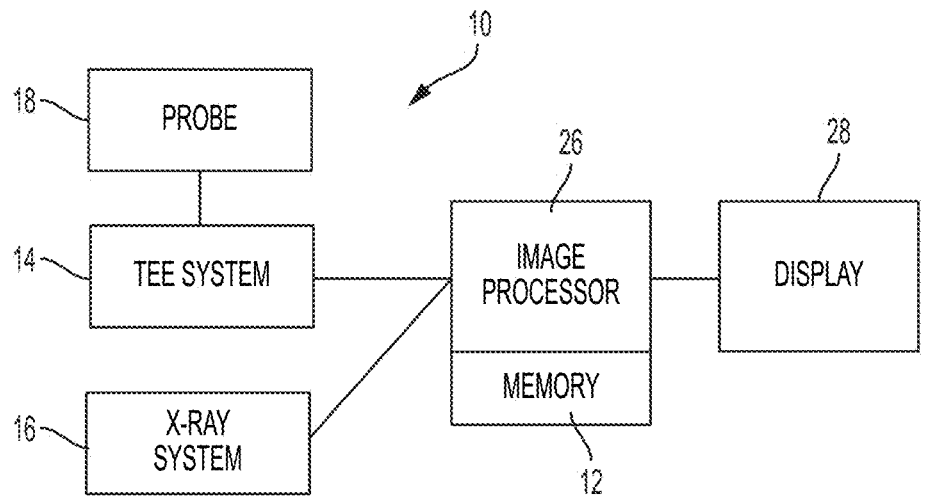
FIG. 1 is a block diagram of one embodiment of a system for pose detection in medical imaging.

FIG. 1 shows a system 10 for pose detection in medical imaging. The system 10 estimates the pose, such as at least 3D location, of the probe 18 from an individual or single x-ray image acquired during intervention and a path of the esophagus. The 3D location of the probe 18 in the x-ray system 16 coordinate space is used for fusion imaging and/or alignment of coordinates.

The system 10 includes a memory 12, a transesophageal echocardiography (TEE) imaging system 14 with an image probe 18, an x-ray system 16, an image processor 26, and a display 28. Additional, different, or fewer components may be provided. For example, a network or network connection is provided, such as for networking with a medical imaging network or data archival system. As another example, a preoperative imaging system, such as a computed tomography or magnetic resonance imaging system, is provided. In another example, a user interface is provided.

The memory 12, image processor 26 and/or display 28 are part of a medical imaging system, such as the x-ray system 16, TEE imaging system 14, or other system. Alternatively, the memory 12, image processor 26, and/or display 28 are part of an archival and/or image processing system, such as associated with a medical records database workstation or server. In other embodiments, the memory 12, image processor 26, and/or display 28 are a personal computer, such as desktop or laptop, a workstation, a server, a network, or combinations thereof. The memory 12, image processor 26, display 28, and/or memory 12 may be provided without other components for implementing the method.

The memory 12 is a graphics processing memory, a video random access memory, a random access memory, system memory, random access memory, cache memory, hard drive, optical media, magnetic media, flash drive, buffer, database, combinations thereof, or other now known or later developed memory device for storing data or video information. The memory 12 is part of an imaging system, a computer associated with the image processor 26, a database, another system, a picture archival memory, or a standalone device.

The memory 12 stores data representing a scan region, at different times, of a patient. The region is a two or three-dimensional region. The region is of any part of the patient, such as a chest, thorax, abdomen, leg, head, arm, or region that is a combination thereof. The data is ultrasound, x-ray, and/or other image data. The data includes x-ray information representing the probe 18 while the probe 18 is within the patient. The data may represent the patient without the probe 18 (i.e., while the probe is not within the patient).

The data is from scanning the region by any medical imaging modality. Any type of data may be used, such as medical image data (e.g., ultrasound, x-ray, computed tomography (CT), magnetic resonance imaging (MRI), or positron emission tomography). In one embodiment, the data representing the patient volume is ultrasound data and x-ray data. The data represents the patient prior to, during, and/or after treatment. For example, the x-ray data is acquired during treatment to guide positioning of the probe and a treatment device (e.g., ablation catheter), and the ultrasound data is also provided during treatment to guide the treatment relative to the soft tissue of the patient. Other medical imaging data (e.g., x-ray, MRI or CT) is acquired prior to treatment or intervention in order to determine the 3D location of the esophagus.

Image data is data that can be used to generate an image, pixels values to be displayed, pixel values that were displayed, or other frames of data representing the region of the patient at a given time. The image data may be frames of DICOM data or frames of data generated along any portion of a data processing path of an imaging system. A sequence of frames of data is acquired, such as acquiring fluoroscopy images over two or more heart cycles at any frame rate (e.g., 10-20 frames per second). Alternatively, one or any number of frames of data are acquired based on trigger events rather than an on-going sequence.

The memory 12 alternatively or additionally stores pose information, such as position, orientation, and/or scale of the probe 18. 2D position and/or 3D position may be stored. Any parameters, thresholds, machine-learnt classifiers, templates, selections, tracking information, transforms, and/or other calculated information for aligning the coordinate systems may be stored.

The memory 12 or other memory is alternatively or additionally a computer readable storage medium storing data representing instructions executable by the programmed processor 26 for detecting probe pose from an x-ray image. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The TEE imaging system 14 is a medical diagnostic ultrasound imaging system built for TEE or used for TEE. In alternative embodiments, the ultrasound system is for imaging with any of various probes, such as a catheter, handheld, or other probe. Using ultrasound, the TEE imaging system 14 scans a plane, planes, and/or volume of the patient from the probe 18. The probe 18 includes a transducer, such as an array of piezoelectric elements, for converting between acoustic and electrical energies for scanning the patient.

The probe 18 is an endocavity probe for insertion into the throat of the patient. By positioning the probe 18 in the esophagus of the patient, the probe 18 may be used to scan the heart or other cardiac region of the patient. In alternative embodiments, the probe 18 is a catheter for insertion into the circulatory system of the patient. The probe 18 is positioned within the patient for ultrasound imaging. The position is spatially limited, such as being in the esophagus or a vessel. The scanning is performed using the probe 18 while the probe 18 is in the patient.

The x-ray system 16 is any now known or later developed x-ray system, such as a C-arm x-ray, fluoroscopy, angiography, or other x-ray system. The x-ray system 16 includes an x-ray source and detector separated by a region into which the patient is positioned. Using a C-arm or other supporting structure, the source and detector are positioned relative to the patient. x-rays generated by the source pass through the patient and the probe 18 if within the patient, and the detector detects the attenuated x-rays. The C-arm may position the source and detector to be at different angles relative to the patient. During an intervention and since single x-ray images may be used for estimating pose over time, the C-arm may keep the source and detector at a given angle relative to the patient. The source and detector are kept at one position during the intervention, but may be moved to other positions before the intervention. Alternatively, the source and detector are moved during the intervention.

By transmitting x-rays through the patient to the detector, a projection image is provided. Any tissue, bone, the probe 18, and/or other medical device along the path of travel of the x-ray beam interacts with the x-rays, causing a detectable difference in intensity at the detector. Since each pixel or location of the detector represents an accumulation of responses along the path of travel, the x-ray image is a projection image of the region.

The x-ray image may be responsive to the probe 18. For example, during surgery or other intervention, the probe 18 may be positioned within the patient for imaging the cardiac system. One or more fluoroscopy images are generated in real-time during the procedure. A sequence of fluoroscopy images over multiple (e.g., three or more) heart cycles is acquired. The fluoroscopy images represent the patient and/or probe 18 in the patient for one or different phases in any one or multiple heart cycles. The frames of the fluoroscopy sequence are acquired and processed for detection within seconds of acquisition (e.g., real-time or on-line detection) or are stored and later retrieved for detection.

The image processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for detecting pose of the probe 18 and/or aligning coordinate systems of the TEE imaging system 14 and the x-ray system 16. The image processor 26 is a single device or multiple devices operating in serial, parallel, or separately. The image processor 26 may be a main processor of a computer, such as a laptop or desktop computer, or may be a processor for handling some tasks in a larger system, such as in an imaging system. The image processor 26 is configured by instructions, design, firmware, hardware, and/or software to be able to perform the acts discussed herein.

Figure 2:
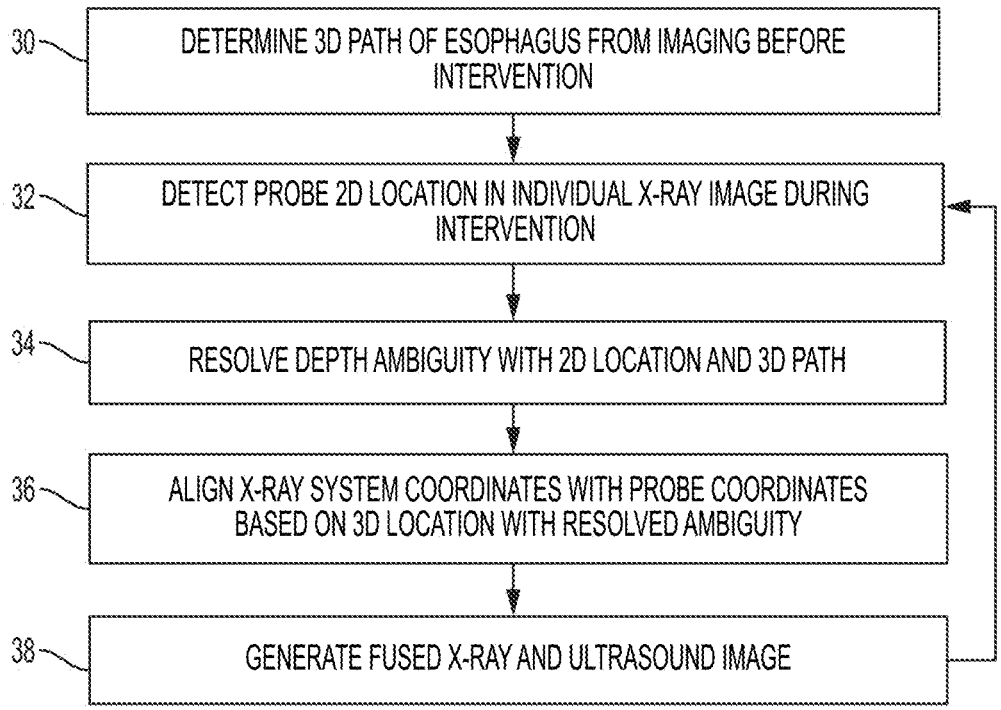
FIG. 2 is a flow chart diagram of one embodiment of a method for detection of a probe pose in x-ray medical imaging.

The acts 30-38 of FIG. 2 or sub-sets thereof are implemented by the image processor 26. Interaction with the TEE system 14 and x-ray system 16 are used to acquire the data representing the patient and/or transducer for determining the pose of the transducer. As compared to the specifics discussed below for FIG. 2, the operation of the image processor 26 is now described in general.

The image processor 26 is configured to detect, separately for each of the x-ray images of a sequence, a 3D location of the transducer relative to the x-ray source. The 3D location is detected from proximity of (a) a line from the transducer as detected in the x-ray image to the position of the x-ray source to (b) a trajectory of an esophagus of the patient. The trajectory is provided to or determined by the image processor 26. The image processor 26 finds the closest points of line (a) with the trajectory (b) as the 3D location. By repeating for each individual x-ray image, dynamic or real-time 3D location detection is provided (i.e., closest points over time are used).

The image processor 26 may determine further pose parameters. In addition to the 3D location, the orientation of the transducer at the 3D location is determined. Based on image processing, the direction at which the transducer faces for scanning (i.e., normal to a center of an emitting face of the transducer) and/or the direction a tip or end of the probe 18 is facing are determined. The x-ray image is processed to determine the orientation. Like the 3D location, this orientation pose information may be determined for each time represented by each x-ray image. The image processor 26 may estimate scale as another pose parameter.

The display 28 is a monitor, LCD, projector, plasma display, CRT, printer, or other now known or later developed devise for outputting visual information. The display 28 receives images, graphics, or other information from the image processor 26, memory 12, TEE system 14, and/or x-ray system 16.

One or more x-ray images representing a probe position relative to a patient region are displayed. The location of the medical device (e.g., probe 18) is or is not highlighted, marked by a graphic, or otherwise indicated on the x-ray image. For example, an image includes fluoroscopic information showing the location of a probe 18. Where a sequence of images is displayed, the location of the probe 18 is shown in each of the images through the sequence. One or more ultrasound images may also be shown. The alignment or position of the ultrasound images relative to the x-ray images is output, represented on the display, or incorporated into the displayed images as fusion imaging. A location of an annotation or selection in one image may be shown in another image based on the aligned coordinate systems (i.e., based on the known position of the probe 18 in the x-ray system 16 coordinate space). Alternatively, the ultrasound and fluoroscopy images are aligned and fused into one image (e.g., ultrasound image overlaid on part or all of the fluoroscopy images) using the alignment based on the identified 3D location.

FIG. 2 shows one embodiment of a method for detection of a probe pose in x-ray medical imaging. Pre-intervention medical imaging is used to determine a path of a patients esophagus. During intervention, a 3D location of the probe at a given time is estimated from a 2D location detected in one x-ray image and the path of the esophagus. For other times during the intervention, other individual x-ray images and the same path of the esophagus are used. In other embodiments, other path restrictive (e.g., tubular or spatially constraining) anatomy may be used instead of the esophagus.

The method is implemented by the system 10 of FIG. 1 or a different system. For example, the x-ray system 16 or other imaging system performs a scan prior to intervention. The image processor 26 or other system, with or without user input, performs act 30 using the results of the scan. The x-ray system 16 performs a scan after intervention begins, and the image processor 26 performs act 32 using the results of the intervention scan. The image processor performs acts 34 and 36 based on the output of acts 30 and 32. The TEE system 14 performs a scan during the intervention, and the image processor 26 performs act 38 based on the TEE scan, the x-ray scan, and the results of act 36. The image processor 26 interacts with the display 28 for performing act 38.

The acts are performed in the order shown (e.g., top to bottom or numerical order) or a different order. Additional, different, or fewer acts may be provided. For example, acts 36 and/or act 38 are not performed. As another example, acts 32-38 are performed repetitively, such as repeating 10-20 times a second during an intervention.

For performing acts 30, 32, and 38, medical imaging data is acquired. The medical imaging data is one or more frames of data from scanning a patient, such as x-ray, CT, MRI, C-arm CT, and/or ultrasound data. Each frame represents a 2D or 3D region of the patient at a given time or over a period. The data is processed or used as the data is acquired. Alternatively, the data is stored and later loaded and processed.

In act 30, x-ray, C-arm CT, CT, MRI, or other medical imaging is used. For act 32, x-ray imaging is used. The x-ray system scans a patient while the probe is within the patient. The probe may also be used to scan the patient, such as with ultrasound for use in act 38. For pose detection, the frames of data from the x-ray system are used with the trajectory determined in act 30 from other or the same modality of medical imaging. The x-ray scanning is repeated any number of times at any rate. For example, a sequence of frames representing the patient and probe at different times is acquired. The sequence is acquired at 10-20 frames per second, but may have a different rate. The sequence is acquired over seconds or minutes.

In act 30, the image processor determines a 3D path of an esophagus of a patient. The determination of the path from imaging data is automatic, such as not using any user input other than to activate and/or select data to be used. The image processor applies segmentation, filtering (e.g., machine-learnt classification), or other image process to identify locations of the esophagus represented in the medical imaging data. Alternatively, a manual or semi-automatic process is used. For example, the user traces the esophagus in one or more images. As another example, the user selects an esophagus location as a seed point, and the image processor determines the location of the esophagus based on the image data and the seed point.

The 3D path is determined from medical imaging prior to an intervention on the patient. During the intervention, the TEE probe is used for imaging soft tissue to guide the intervention or treatment. The intervention begins by inserting a treatment device into the patient, such as a catheter for ablation. The patient is sedated and placed on an examination table or gurney. Once the patient is ready, the TEE probe and treatment device are inserted into the patient in any order. This insertion is the beginning of the intervention. Alternatively, the intervention begins once the treatment device is positioned in the organ with the location to be treated (e.g., in the heart). In yet another alternative, the intervention begins when the TEE probe is positioned so that the location to be treated may be imaged. The 3D path is determined prior to beginning the intervention. In an alternative embodiment, the 3D path is determined prior to use to determine the 3D location of the probe regardless of whether the intervention has begun.

The 3D path is determined as a trajectory along which a probe is to be inserted into a patient. Any range of the esophagus may be included in the trajectory, such as from a top of the torso (e.g., shoulder) to the stomach or a point below the heart if the patient were standing. The trajectory is determined in three-dimensions relative the patient. In a world coordinate system or a coordinate system of the x-ray system, the path is found. The path is defined by sampling locations in 3D, such as x, y, z coordinates. Alternatively, the path is found by a line fitting where the line may be represented by discrete coordinate values.

The path is determined as a tube. For example, an inner, outer, or both inner and outer tissue of the esophagus are detected. In another example, a centerline of the esophagus is determined as the path. Based on detection of the esophagus tissue, a shrinking or other centerline operation is used to determine the centerline as the path.

Figure 3:
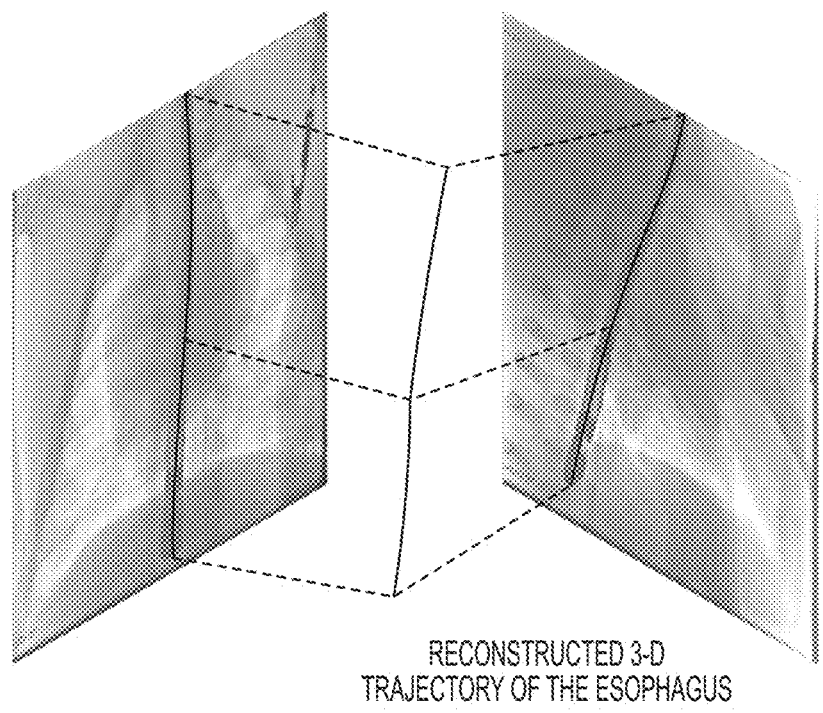
FIG. 3 illustrates one embodiment for determining a trajectory of an esophagus.

In one embodiment represented in FIG. 3, the 3D trajectory of the esophagus is extracted based on imaging after the patient is on the table under general anesthesia. Before the intervention starts, the TEE probe is inserted into the esophagus and placed deeper than the heart, such as near the entrance of the stomach. With the probe in this position, the patient is scanned from different directions with the x-ray source. The C-arm moves the x-ray source and detector to different angles relative to the patient. FIG. 3 shows projection images generated from scanning form two different angles. Any angles may be used, such as 45 or 90 degrees apart. The x-ray images are of the thorax or chest region of the patient.

The esophagus is located in each of x-ray scan images resulting from the scanning from different directions. For example, thresholding, template matching, or segmentation is applied to find the TEE probe (e.g., elongated body of the TEE probe) in the esophagus. The centerline of the esophagus is then determined from the detected TEE probe. FIG. 3 shows detection of the centerline in each of the x-ray images. These centerlines provide 2D distribution of the esophagus as viewed from two different directions. In another approach, the esophagus is determined without using the TEE probe to increase contrast.

The 3D path of the esophagus is reconstructed from the locations of the esophagus in each of the scan images. The 2D centerlines viewed from different directions geometrically relate to each other. By reconstructing this relationship, the 3D path is determined as shown in FIG. 3. The 2D centerlines from two different angles are combined to reconstruct the 3D centerline as the 3D trajectory of the esophagus.

Because determining the path of the esophagus is performed only once and before the interventional procedure starts, rotating the C-arm to acquire two or more x-ray images from different angles may be more easily managed and acceptable to clinicians. In alternative embodiments, the path is determined multiple times. The paths are averaged or used for different phases of the cardiac cycle.

In another embodiment, pre-operative 3D imaging is used to determine the 3D path of the esophagus. Using x-ray (e.g., C-arm CT), MRI, or CT, data representing a volume of the patient including the esophagus is acquired. This pre-operative volume may be acquired the same day as or a different day as the intervention. The esophagus is located in the volume using image processing and/or manual input (e.g., tracing).

To relate the pre-operative volume to the coordinate system of the x-ray system used in the intervention, the patient is scanned from different directions with the x-ray source without the TEE probe being in the patient. After the patient is on the table under general anesthesia for the intervention but before inserting the TEE probe into the patients esophagus, two or more x-ray images are acquired from different angles, such as 45 or 90 degrees apart. The chest or thorax region is scanned for each of the x-ray images.

The x-ray images are spatially registered with the pre-operative volume representing the patient. The volume is projected to model the x-ray projection images. The projection is performed from different angles and/or scales. Each projection is then fit with the x-ray images. Any measure of similarity may be used, such as a cross-correlation or minimum sum of absolute differences. The angles and scales with the projection most similar to the x-ray images from the different angles are determined.

These angles and scales for the different directions relate the coordinate system of the pre-operative volume to the x-ray system. The 3D path of the esophagus from the pre-operative volume is then transformed to the coordinate system of the x-ray system. The 3D path is determined from the esophagus as labeled in the pre-operative volume and the spatially registering. The registration brings the extracted 3D trajectory of the esophagus into the patient coordinate system or coordinate system of the x-ray system.

In yet another embodiment, the x-ray system of the intervention is used to acquire the volume, so registration may be avoided. A 3D volume representing the patient is acquired using the x-ray source. An intra-operative C-arm CT volume is acquired prior to the intervention. The patient is sedated and positioned on the table in preparation for the intervention. Prior to the intervention, a C-arm CT scan is performed, resulting in a volume representing the patient.

The 3D path of the esophagus as represented in the 3D volume is determined. The volume is used for the extraction of the 3D trajectory of the patients esophagus. The esophagus is found by tracing, seeded imaging processing, thresholding, segmentation, filtering, classification, or other approach. In this case, the C-Arm CT volume is by default registered properly with the patient so that an additional registration does not need to be performed. The 3D path is in the coordinate system of the x-ray system.

Figure 4:
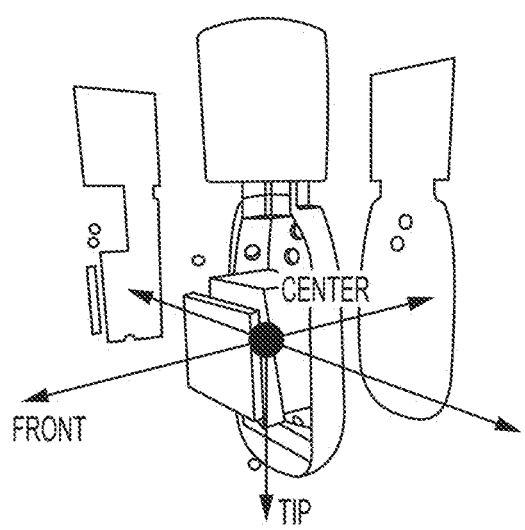
FIG. 4 illustrates probe pose parameters according to one embodiment.

In act 32, the image processor detects a pose of the TEE probe from an x-ray image acquired during the intervention on the patient. The pose is a position with or without orientation and/or scale. FIG. 4 shows an example probe and two vectors for orientation. The center represents a location in three dimensions, such as x, y, z location. The "front" vector represents an orientation of the emitting face of the transducer in the probe head. The "tip" vector represents an orientation of the tip of the TEE probe or the direction of travel of the TEE probe through the esophagus. The front and tip vectors are restricted to be orthogonal, but other relationships may be used. Other location, orientation, and/or scale parameterizations may be used. For example, orientation is parameterized as three Euler angles (e.g., yaw, roll, and/or pitch).

The pose of the TEE probe is detected using any of various image processes. For example, a machine-learnt classifier or detector is applied to the x-ray frame of data to detect the pose. Using input features, the machine-learnt detector finds the location, orientation, and/or scale based on a learned relationship between the input feature vectors and pose. A hierarchy of machine-learnt detectors may be used, such as finding location, then orientation, and then scale with the sequence of detectors boot-strapped together. As another example, template matching is used to detect the pose. Representative templates of the head of the TEE probe at different orientations are correlated with the x-ray image at different positions. The location with the greatest correlation indicates location. The orientation of the template with the greatest correlation indications the orientation. The scale of the located and oriented template with the greatest correlation indicates the scale. Combinations of approaches may be used. Any now known or later developed approach to detect pose from the x-ray image may be used.

A single x-ray image is used to determine the pose at a given time. The x-ray image is acquired during the intervention. After the TEE probe is inserted for use to scan the tissue and guide the treatment or after beginning the intervention, an x-ray image is acquired to determine the location of the TEE probe in the patient. The detection of the pose is performed for the given x-ray image independently of or without also using another x-ray image. X-ray images from different times during the intervention and/or from different angles are not used in the detection of the pose. In alternative embodiments, a pose from a previous detection is used to guide or provide a starting point for finding the pose in the current detection, but the x-ray images are from the same viewing direction and the detection is performed in just the current x-ray image.

While a single image and/or view direction is used, the detection is repeated using other x-ray images. As each x-ray image in a sequence is acquired, a pose is determined for each of the individual one of the x-ray images. This provides a sequence of poses over time.

In a given or individual x-ray image, the location is provided in two dimensions. The location of the TEE probe is detected as a point in the projection plane. The TEE probe has a point parameterized as the location of the transducer or head of the TEE probe. In the example, of FIG. 4, the center of the head is used. The tip, center of the transducer array, or other location on the TEE probe may be used as the location.

Figure 5:
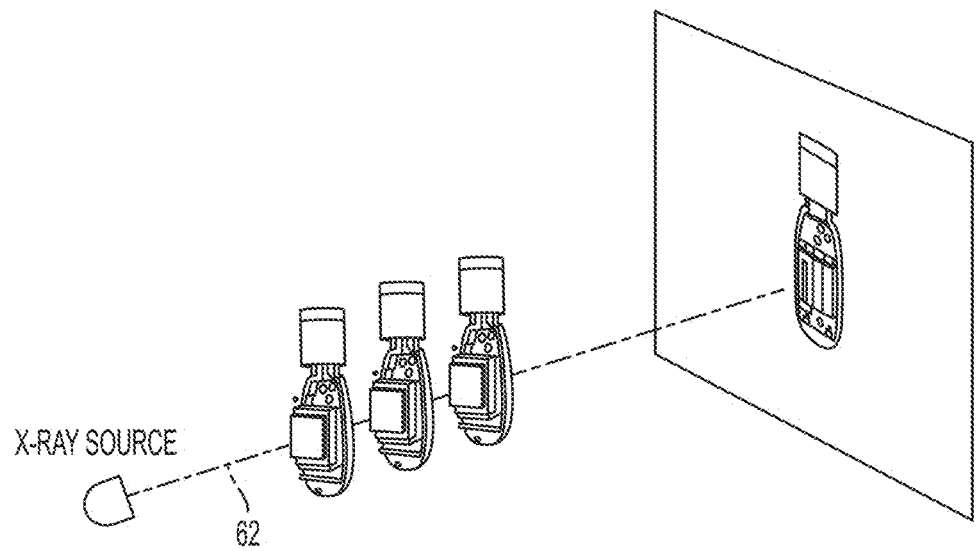
FIG. 5 illustrates an example of depth ambiguity based on detection of probe location in one x-ray image.

The orientation, scale, and 2D location are detectable from the single x-ray image. This 2D location is ambiguous in the third dimension. FIG. 5 shows detection of the location in two dimensions with ambiguity along a third dimension. The projection of the x-ray image collapses the third dimension corresponding to a view direction from an x-ray source. While the location in the 2D projection plane of the x-ray image is detected, the location of the TEE probe along the depth relative to the x-ray source is not known, is uncertain, or may not be accurately detected by image processing the x-ray image. The location of the TEE probe along a line 62 extending from the x-ray source to the 2D location in the x-ray image represents possible depths for the TEE probe. The depth ambiguity means that the position of the TEE probe is uncertain along the viewing direction.

In act 34, the image processor resolves the ambiguity along the third dimension with the 3D path of the esophagus. The z or depth location in the Cartesian system of the x-ray system is determined so that a depth (z) of the 3D location (x, y being in the projection plane) is estimated. Where the Cartesian or other coordinate system being used does not align with the x-ray system, the projection plane provides location with ambiguity along one direction and the ambiguity along this one direction is resolved with the 3D path.

The resolution of the location provides the location in three dimensions. The 2D location from the projection x-ray image is resolved into a 3D location, including depth along the line from the x-ray source to the 2D location. For example, the center of the TEE probe detected in the 2D x-ray image or projection plane is resolved to a location in three dimensions (location in two dimensions and a location in the third dimension).

The location in three dimensions is detected from the detected location in two dimensions in the individual x-ray image and from the trajectory (e.g., path of the esophagus). The depth ambiguity is resolved by combining the detected 3D pose (e.g., orientation+2D location with depth ambiguity) with the 3D trajectory of the esophagus.

Figure 6:
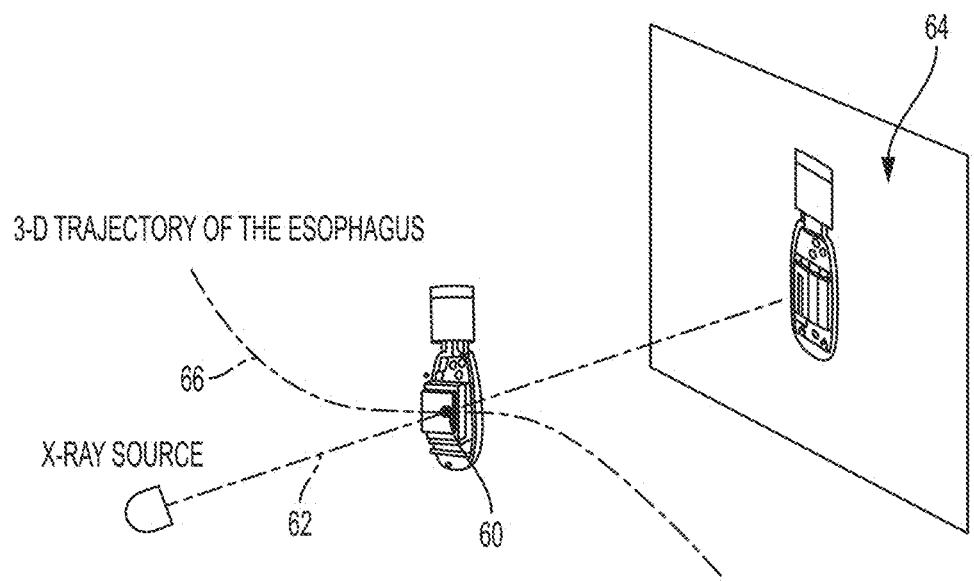
FIG. 6 illustrates resolution of the depth ambiguity in the example of FIG. 5 using the trajectory of the esophagus.

FIG. 6 shows one embodiment of resolving the depth. The point 60 is determined as the 3D location, including the depth. This point represents the 3D location of the TEE probe, such as being a 2D location of the TEE probe in the projection plane or x-ray image 64 plus a depth relative to the x-ray source. To find the point 60, a line 62 passing through the x-ray source and the 2D location in the projection plane or x-ray image 64 is calculated. The point 60 is calculated as the location along the line 62 having a shortest distance to the 3D path 66 of the esophagus. For example, the line 62 connecting the center of the TEE probe detected from the x-ray image 64 and the center of the x-ray source provides possible positions of the center of the TEE probe. The center of the TEE probe should also be within the esophagus. Combining this information, the point along the line 62 with the shortest distance to the 3D trajectory (i.e., path 66) of the esophagus is selected as the center of the TEE probe. Since the 3D trajectory is provided in the x-ray or patient coordinate system, the location on the line 62 closest to the path 66 indicates the depth of the TEE probe. The shortest distance is found as a Euclidian distance, but other measures may be used. This closest approach between the line 62 and the 3D path 66 resolves the depth ambiguity.

The location in three dimensions is determined based on detection in a single or individual x-ray image. By detecting the probe location in the 2D x-ray image, the 3D location may be resolved using the trajectory. The detection for 2D location is performed only in one x-ray image for a given time during the intervention. The 3D path 66 of the esophagus is used to resolve depth ambiguity without needing an image from a different direction, allowing real-time 3D location detection. The same 3D path 66 may be used with other detections in other x-ray images 64 for other times during the intervention. In other embodiments, more than one x-ray image 64 may be used for detection of location at a given time.

Referring again to FIG. 2, the image processor aligns coordinates between the x-ray source and the TEE probe based on the 3D location of the TEE probe in the x-ray coordinate system. A spatial transform between the x-ray source and the TEE probe provides the alignment. The 3D location is a pose or part of a pose of the probe relative to the x-ray system. The 3D location provides a transform relating the two systems. The position of the ultrasound image in the coordinate system of the probe may be related to or aligned with the position of the x-ray image in the coordinate system of the x-ray system.

The alignment may be used to inform the physician of probe position relative to the patient and/or ultrasound image relative to the x-ray image. The alignment allows for fusion of different types of images, fusion by indication of the spatial relationship (e.g., position, orientation, and/or scale) between the types of images, and/or fusion by cross-reference between modalities of annotation, marking, or detection.

The pose of the probe in each frame of x-ray data provides the spatial relationship between the x-ray system and the ultrasound system of the probe. In one embodiment, a 3D point $Q_{TEE}$ in the ultrasound coordinate system is projected in the x-ray image at 2D image point $Q_{Fluoro}$. The relationship is represented as:

$$Q_{fluoro} = P_{int} P_{ext} (R_{TEE}^W Q_{TEE} + T_{TEE}^W)$$

where $P_{int}$ is x-ray or camera internal projection matrix, $P_{ext}$ is x-ray camera external matrix that transforms a point from a world coordinate to camera coordinate system. The internal and external relate the movable C-arm mounted x-ray and detector space to the world space of the x-ray system. The internal and external matrices are known from calibration and C-Arm rotation angles. The ultrasound system, including the probe, are also defined in the world space. $R_{TEE}^W$ and $T_{EE}^W$ are the rotation and position of the TEE probe in the world coordinate system. $R_{TEE}^W$ and $T_{TEE}^W$ are computed from:

$$R_{TEE}^W = P_{ext}^{-1} R_{TEE}^C$$

$$T_{TEE}^W = P_{ext}^{-1} T_{TEE}^C$$

where $R_{TEE}^C$ and $T_{TEE}^C$ are the rotation and position of the TEE probe in the x-ray coordinate system. $R_{TEE}^C = (\theta_z, \theta_x, \theta_y)$, and $T_{TEE}^C = (x; y; z)$. By detection of the pose, the relationship may be determined. Other transforms, such as between the internal x-ray space and the ultrasound space without reference to the world space, may be used.

The poses over time are used to align the coordinates of the x-ray system with the probe over time. The alignment occurs for each time. Alternatively, an average transform is calculated and used for subsequent registration, transformation, or conversion.

In act 38, the image processor generates a fused image from the x-ray image and an image generated using the TEE probe. The 3D location is used to create the transform, which may then be used to association a location in one image to a corresponding location in another image (e.g., selection of a tissue location in an ultrasound image results in indication of the tissue location in the x-ray image). Other fused medical imaging, such as displaying adjacent x-ray and ultrasound, may be used.

In one embodiment, the image processor generates a fused image from one of the frames of data from the x-ray system and an image generated using the TEE probe. Using the alignment, the spatial locations represented by one type of imaging are transformed to coordinates of another type of imaging. This alignment may be used to create a display with two types of images shown side-by-side. The perceived relative positioning is based on the alignment, helping the viewer understand the relationship. Alternatively or additionally, one type of imaging is transformed into the coordinates of another type and overlaid. For example, a fluoroscopy image is displayed as a gray-scale image. For a region in the gray-scale image, ultrasound data replaces the fluoroscopic data or the fluoroscopic data is overlaid by an ultrasound image. The ultrasound image may be in color. Any now known or later developed display of images from two types of imaging using relative alignment may be used. In other embodiments, the detected probe may be highlighted in an image, such as by modulating the brightness, overlaying a graphic of the probe, or coloring the pixels of the probe.

As an alternative to fusion of images or as a use for fused imaging, the coordinate systems of the two systems (e.g., x-ray and ultrasound) are aligned. Landmarks selected by a physician in the ultrasound (3D) are transferred or relatable to an x-ray image (2D). Those overlaid landmarks are bio-markers guiding the physician during intervention. While fusion of images may not occur, the images from both types of imaging and the coordinate alignment assist in guiding the physician as a form of fusion imaging. The fusion imaging uses the transform to relate images, either by overlay, adjacent display with alignment, and/or related marking.

As represented by the arrow from act 38 to act 32, the detection of the pose with 2D location, resolving depth ambiguity to provide 3D location, alignment of the coordinates, and generation of the fused image are repeated. The detection and resolving of acts 32 and 34 are performed with a different individual x-ray image. As each x-ray image is acquired, the 3D position of the probe is determined. The sequence of x-ray images acquired during the intervention are used to determine pose, including 3D position, of the TEE probe over time. For each time, an individual x-ray image is used to find the pose. The trajectory may be based on other x-ray images or other medical imaging from before the intervention, but each pose determined during the intervention uses detection of the probe in a single one of the x-ray images of the sequence. Using previous poses to initialize the search for detection still provides for detection in that single x-ray image for a given pose. This may allow for real-time (e.g., 10 frames per second or more) tracking of the probe pose and alignment of the coordinate systems. Different individual frames of x-ray data are used to determine pose at different times.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for detection of a probe pose in x-ray medical imaging, the method comprising:
    determining, from medical imaging prior to an intervention on a patient, a three-dimensional path of an esophagus of the patient;
    detecting an orientation and a first location of a trans-esophageal echocardiographic (TEE) probe during the intervention on the patient from a single x-ray image acquired during the intervention, the first location including two dimensions with depth ambiguity along a third dimension corresponding to a view direction from an x-ray source used for the single x-ray image;
    resolving, the depth ambiguity along the third dimension using the three-dimensional path, the resolving providing a second location in the three dimensions; and
    aligning coordinates of the x-ray source with the trans-esophageal echocardiographic (TEE) probe based on the second location.

2. The method of claim 1 wherein determining comprises determining the three-dimensional path of the esophagus as a centerline of the esophagus.

3. The method of claim 1 wherein determining comprises:
    scanning the patient from different directions with the x-ray source while the trans-esophageal echocardiographic (TEE) probe extends in the esophagus past a heart of the patient;
    locating the esophagus in each of scan images resulting from the scanning from different directions; and
    reconstructing the three-dimensional path of the esophagus from locations of the esophagus in each of the scan images.

4. The method of claim 1 wherein determining comprises:
    scanning the patient from different directions with the x-ray source without the trans-esophageal echocardiographic (TEE) probe being in the patient;
    spatially registering scan images resulting from the scanning from different directions with a pre-operative three-dimensional volume representing the patient; and
    determining the three-dimensional path from an esophagus labeled in the pre-operative three-dimensional volume and the spatially registering.

5. The method of claim 1 wherein determining comprises:
    acquiring a three-dimensional volume representing the patient using the x-ray source; and
    determining the three-dimensional path as represented in the three-dimensional volume.

6. The method of claim 1 wherein detecting comprises detecting the first location as a point in a projection plane of the single x-ray image of the trans-esophageal echocardiographic (TEE) probe within the patient and the orientation as a vector of a front and tip of the trans-esophageal echocardiographic (TEE) probe.

7. The method of claim 1 wherein detecting comprises detecting with a machine learnt detector.

8. The method of claim 1 wherein detecting comprises detecting the first location and orientation in a projection plane of the single x-ray image.

9. The method of claim 1 wherein resolving comprises finding a point along a line that passes through the x-ray source and through the first location, the second location being at the point.

10. The method of claim 9 wherein resolving comprises selecting the point as being on the line and having a shortest distance to the three-dimensional path.

11. The method of claim 1 wherein detecting provides a center of the trans-esophageal echocardiographic (TEE) probe as the first location in the two dimensions and wherein the resolving provides the center of the trans-esophageal echocardiographic (TEE) probe as the second location in the three dimensions, the second location being the first location in the two dimensions and a position in the third dimension.

12. The method of claim 1 wherein aligning comprises calculating a transform between the x-ray source and the trans-esophageal echocardiographic (TEE) probe.

13. The method of claim 1 further comprising repeating detecting and resolving during the intervention without repeating the determining.

14. The method of claim 1 further comprising generating a fused image from the single x-ray image and an image generated using the trans-esophageal echocardiographic (TEE) probe.

15. A method for detection of a probe pose in x-ray medical imaging, the method comprising:
    determining, prior to an intervention, a trajectory along which a probe is to be inserted into a patient, the trajectory being in three-dimensions relative to the patient;

acquiring, during the intervention, an individual x-ray image of the patient with the probe within the patient;

detecting a location of the probe in two dimensions from the individual x-ray image of the patient with the probe within the patient;

detecting the location of the probe in three dimensions from the detection of the location in the two dimensions from the individual x-ray image and the trajectory; and performing fused medical imaging with the probe and x-ray imaging based on the location in the three dimensions.

16. The method of claim 15 wherein determining the trajectory comprises determining a path of an esophagus of the patient, and wherein detecting the location in three dimensions comprises calculating a point along a line from an x-ray source for the individual x-ray image to the location in the two dimensions with a closest approach to the path.

17. The method of claim 15 wherein determining the trajectory comprises determining prior to beginning an intervention guided by imaging with the probe, and further comprising repeating the detecting the location in the two dimensions and detecting the location in the three dimensions with a different individual x-ray image acquired during the intervention.

18. A system for detection in medical imaging, the system comprising:

a transesophageal echocardiography imaging system comprising a transducer for imaging with ultrasound from within a patient;

an x-ray system configured to acquire a sequence of x-ray images with an x-ray source in one position relative to the patient during an intervention, the x-ray images representing the patient and the transducer over time; and an image processor configured to detect, separately for each of the x-ray images, a three-dimensional location of the transducer relative to the x-ray source, the three-dimensional location detected from proximity of (a) a line from the transducer as detected in a respective x-ray image to the position of the x-ray source to (b) a trajectory of an esophagus of the patient.

19. The system of claim 18 wherein the image processor is further configured to determine, from each of the x-ray images, an orientation of the transducer at the respective three-dimensional location.

20. The system of claim 18 wherein the image processor is configured to detect the three-dimensional locations for the x-ray images as a closest point of the line with the trajectory.

* * * * *